(12) United States Patent
Nessa et al.

(10) Patent No.: US 9,846,850 B2
(45) Date of Patent: Dec. 19, 2017

(54) CONSOLIDATION OF HEALTHCARE-RELATED SCHEDULES ACROSS DISPARATE SYSTEMS

(75) Inventors: Kristine Marie Nessa, Kansas City, MO (US); Karen Ramsey, Lenexa, KS (US); Bryan Muehlmeier, Overland Park, KS (US); Susan Marie Stiles, Lake Tapawingo, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 252 days.

(21) Appl. No.: 12/982,333

(22) Filed: Dec. 30, 2010

(65) Prior Publication Data

US 2012/0173279 A1 Jul. 5, 2012

(51) Int. Cl.
| | | |
|---|---|---|
| *G06Q 50/00* | (2012.01) | |
| *G06Q 10/00* | (2012.01) | |
| *G06Q 10/06* | (2012.01) | |
| *G06Q 50/22* | (2012.01) | |
| *G06Q 50/24* | (2012.01) | |

(52) U.S. Cl.
CPC ..... *G06Q 10/063118* (2013.01); *G06Q 50/22* (2013.01); *G06Q 50/24* (2013.01)

(58) Field of Classification Search
CPC ........... G06Q 10/063118; G06Q 50/22; G06Q 50/24; G06Q 10/06
USPC .......................................................... 705/3
See application file for complete search history.

(56) References Cited

U.S. PATENT DOCUMENTS

| | | | | |
|---|---|---|---|---|
| 7,689,441 | B1* | 3/2010 | Craft | G06F 19/327 600/300 |
| 7,756,728 | B2* | 7/2010 | Maughan et al. | 705/3 |
| 8,271,294 | B2* | 9/2012 | Eisenberger et al. | 705/2 |
| 8,935,753 | B1* | 1/2015 | Cha | G06F 19/327 709/207 |
| 2004/0220836 | A1* | 11/2004 | Doherty et al. | 705/3 |
| 2005/0154627 | A1* | 7/2005 | Zuzek et al. | 705/10 |
| 2005/0187794 | A1* | 8/2005 | Kimak | 705/3 |
| 2005/0215867 | A1* | 9/2005 | Grigsby et al. | 600/300 |
| 2007/0150311 | A1* | 6/2007 | Lazerus | 705/2 |
| 2007/0186106 | A1* | 8/2007 | Ting et al. | 713/168 |
| 2011/0166883 | A1* | 7/2011 | Palmer et al. | 705/3 |

\* cited by examiner

*Primary Examiner* — Hiep V Nguyen
(74) *Attorney, Agent, or Firm* — Shook, Hardy & Bacon L.L.P.

(57) ABSTRACT

Subject matter described herein is related to providing a consolidated schedule having event entries that originate from disparate systems. For example, a central repository receives event entries from a plurality of disparate systems and aggregates entries associated with a particular clinician. The aggregated entries are transformed into a consolidated schedule, which is provided to a client device (e.g., mobile computing device or desktop computing device) used by the healthcare clinician (e.g., doctor, nurse, physician assistant, nurse practitioner, etc.). The consolidated schedule includes events scheduled to take place at different healthcare facilities or different departments within a healthcare facility. When viewing the consolidated schedule, the clinician can request patient information (e.g., vital statistics) relevant to a selected entry and execute other actions (e.g., rescheduling, note entry, event creation, etc.) relevant to the entry.

15 Claims, 5 Drawing Sheets

CONSOLIDATION OF HEALTHCARE-RELATED SCHEDULES ACROSS DISPARATE SYSTEMS

BACKGROUND

A healthcare cluster (e.g., a department or unit within a hospital, a hospital, or a system of hospitals) typically maintains some form of schedule, which tracks events that are planned to take place at the cluster. For example, a department within a hospital might maintain both a schedule of patient appointments, as well as a schedule of healthcare-clinician shift assignments. Healthcare clusters often do not combine schedules with one another to form an integrated schedule and instead maintain separate schedules.

Healthcare clinicians often participate in events that are scheduled in different healthcare clusters. For example, a clinician might be scheduled to participate in multiple procedures in a single day, the multiple procedures taking place in different healthcare facilities or in different departments within the same healthcare facility. Accordingly, it would be useful to provide the healthcare clinician with a consolidated schedule of events to which the clinician is scheduled to attend.

SUMMARY

A high-level overview of various aspects of the invention are provided here for that reason, to provide an overview of the disclosure and to introduce a selection of concepts that are further described below in the detailed-description section below. This summary is not intended to identify key features or essential features of the claimed subject matter, nor is it intended to be used as an aid in isolation to determine the scope of the claimed subject matter.

In brief and at a high level, this disclosure describes, among other things, ways to provide a consolidated schedule having event entries that originate from disparate systems (e.g., scheduling systems, electronic-medical-record systems, etc.). For example, a central repository receives event entries from a plurality of disparate systems and aggregates entries associated with a particular clinician. The aggregated entries are transformed into a consolidated schedule, which is provided to a client device (e.g., mobile computing device or desktop computing device) used by the healthcare clinician (e.g., doctor, nurse, physician assistant, nurse practitioner, etc.). The consolidated schedule includes events scheduled to take place at different healthcare facilities or different departments within a healthcare facility. When viewing the consolidated schedule, the clinician can request patient information (e.g., vital statistics) relevant to a selected entry and execute other actions (e.g., rescheduling, note entry, event creation, etc.) relevant to the entry.

BRIEF DESCRIPTION OF THE SEVERAL VIEWS OF THE DRAWINGS

Illustrative embodiments of the present invention are described in detail below with reference to the attached drawing figures, wherein.

DETAILED DESCRIPTION

The subject matter of select embodiments of the present invention is described with specificity herein to meet statutory requirements. But the description itself is not intended to define what is regarded as the invention, which is what the claims do. The claimed subject matter might be embodied in other ways to include different steps or combinations of steps similar to the ones described in this document, in conjunction with other present or future technologies. Terms should not be interpreted as implying any particular order among or between various steps herein disclosed unless and except when the order of individual steps is explicitly stated.

An embodiment of the invention is directed to providing a consolidated schedule having event entries that originate from disparate systems (e.g., scheduling systems, electronic-medical-record systems, etc.). For example, a central repository receives event entries from a plurality of disparate systems and aggregates entries associated with a particular clinician and/or a particular patient. The aggregated entries are transformed into a consolidated schedule, which is provided to a client device (e.g., mobile computing device or desktop computing device) used by the healthcare clinician (e.g., doctor, nurse, physician assistant, nurse practitioner, etc.) or the patient. The consolidated schedule includes events scheduled to take place at different healthcare facilities or different departments within a healthcare facility. When viewing the consolidated schedule, the clinician can request patient information (e.g., vital statistics) relevant to a selected entry and execute other actions (e.g., rescheduling, note entry, event creation, etc.) relevant to the entry.

Figure 1:
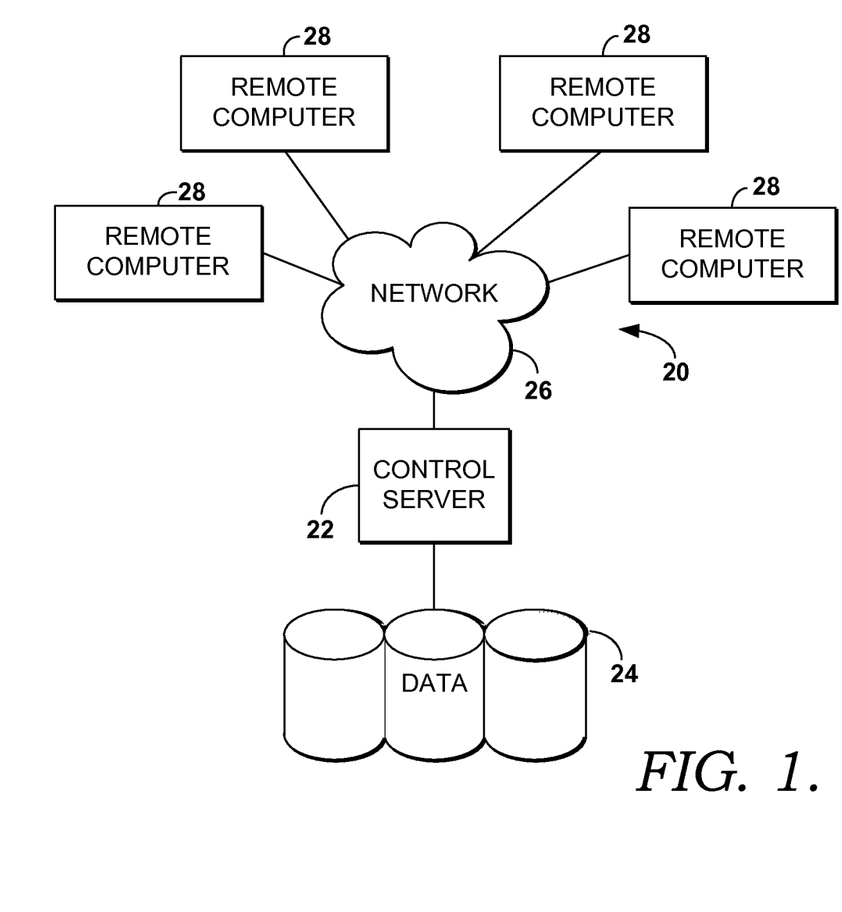
FIG. 1 is a block diagram of an exemplary computing environment suitable for use in implementing an embodiment of the present invention.

Having briefly described an embodiment of the present invention, referring to FIG. 1, an exemplary computing-system environment (e.g., a medical information computing system) in which embodiments of the present invention might be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use, or functionality of, the invention. Neither should the medical information computing system environment 20 be interpreted as having any dependency or requirement relating to any single component or combination of components illustrated therein.

Embodiments of the present invention might be operational with numerous other general purpose or special purpose computing system environments or configurations. Examples of well-known computing systems, environments, and/or configurations that might be suitably used with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention might be described in the general context of computer-executable instructions, such as program modules, being executed by a computer. Generally, program modules include routines, programs, objects, components, and data structures that perform particular tasks or implement particular abstract data types. Embodiments of the present invention might also be practiced in distributed computing environments in which tasks are performed by remote processing devices that are linked through a communications network. In a distributed computing environment, program modules might be located in local and/or remote computer storage media including memory storage devices.

With continued reference to FIG. 1, the exemplary medical information computing system environment 20 includes a general purpose computing device in the form of a server 22. Components of the server 22 might include a processing unit, internal system memory, and a suitable system bus for coupling various system components, including database cluster 24, with the server 22. The system bus might be any of several types of bus structures, including a memory bus or memory controller, a peripheral bus, and a local bus, using any of a variety of bus architectures. Exemplary architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. Computer readable media might include computer storage media, such as volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 might operate in a computer network 26 using logical connections to one or more remote computers 28. Remote computers 28 might be located at a variety of locations in a medical or research environment, including clinical laboratories, hospitals and other inpatient settings, veterinary environments, ambulatory settings, medical billing and financial offices, hospital administration settings, home health care environments, and clinicians' offices. Clinicians include a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. The remote computers 28 might also be physically located in non-traditional medical care environments so that the entire health care community is capable of integration on the network. The remote computers 28 might include personal computers, servers, routers, network PCs, peer devices, other common network nodes, or the like, and might include some or all of the components described above in relation to the server 22. The devices can be personal digital assistants or other like devices.

Exemplary computer networks 26 include local area networks (LANs) and/or wide area networks (WANs). Such networking environments are commonplace in offices, enterprise-wide computer networks, intranets, and the Internet. When utilized in a WAN networking environment, the server 22 might include a modem or other means for establishing communications over the WAN, such as the Internet. In a networked environment, program modules or portions thereof might be stored in the server 22, in the database cluster 24, or on any of the remote computers 28. For example, various application programs might reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user might enter commands and information into the server 22 or convey the commands and information to the server 22 via one or more of the remote computers 28 through input devices, such as a keyboard, a pointing device (commonly referred to as a mouse), a trackball, or a touch pad. Other exemplary input devices include microphones, satellite dishes, scanners, or the like. Commands and information might also be sent directly from a remote healthcare device to the server 22. In addition to a monitor, the server 22 and/or remote computers 28 might include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 2:
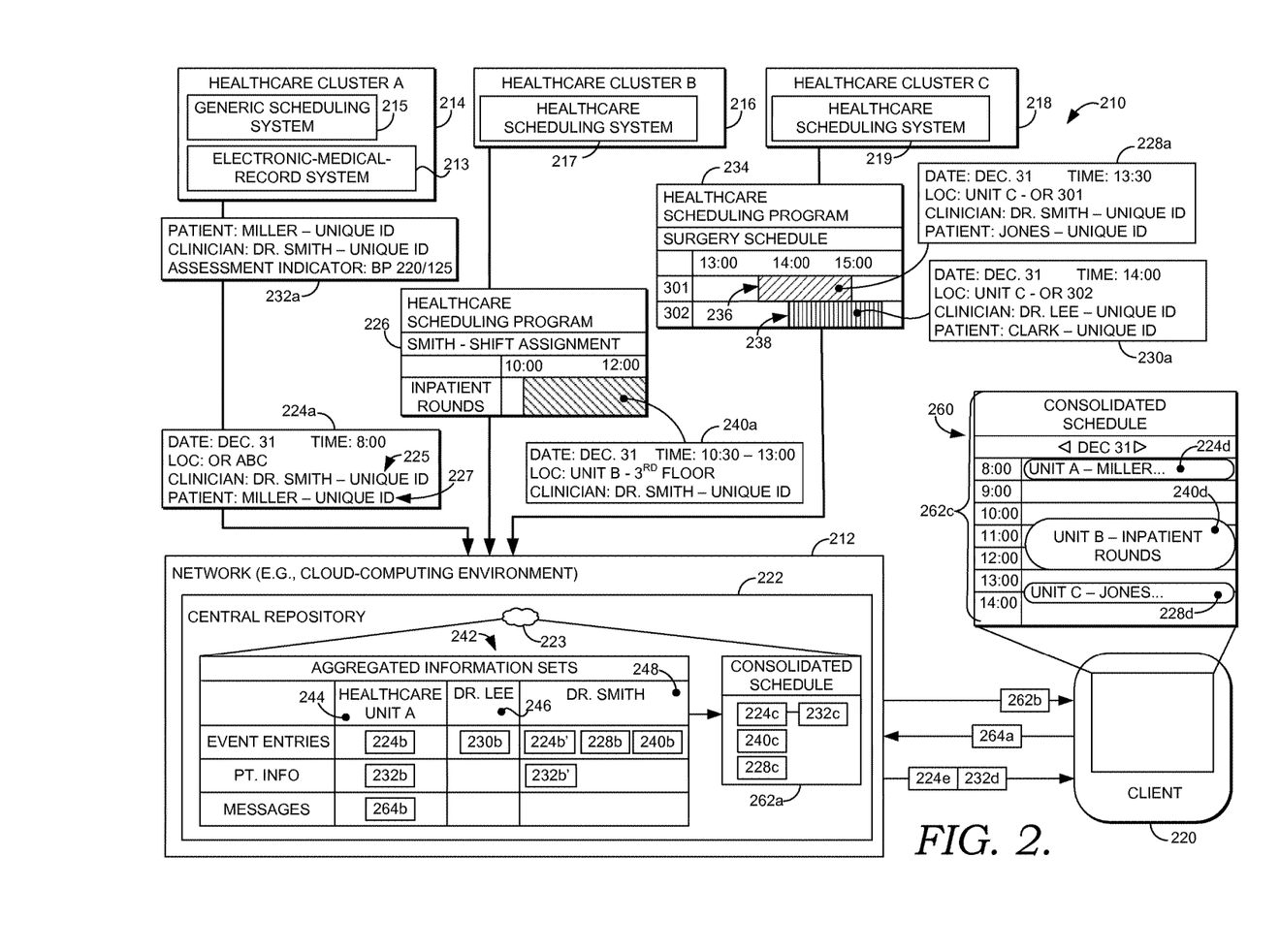
FIG. 2 is a block diagram of an exemplary computing environment suitable for use in implementing an embodiment of the present invention.

Referring now to FIG. 2, another computing environment is described and is identified generally by reference numeral 210. Computing environment 210 might include some or all of the components describe in FIG. 1. The computing environment 210 includes various components that communicate by way of network 212. For example, healthcare cluster A 214, healthcare cluster B 216, and healthcare cluster C 218 might communicate with client device 220 (e.g., mobile computing device, desktop, laptop, tablet, PDA, etc.) by way of network 212. Network 212 includes a set of computing resources (e.g., servers, storage, bandwidth, software, etc.) that facilitate communication between the various components of environment 210 and deploy various hosted applications. For example, network 212 might include a cloud-computing environment.

Computing environment 210 includes disparate healthcare clusters A, B, and C. A "disparate healthcare cluster" includes a group of healthcare-related resources (e.g., clinicians, staff, equipment, supplies, computing devices, etc.) that are used to provide healthcare services. Examples of a disparate healthcare cluster include a department or unit within a healthcare facility; a healthcare facility (e.g., hospitals, clinics, private physician offices, etc.); and a system of healthcare facilities. Sometimes, disparate healthcare clusters are controlled by respective healthcare financial institutions.

A disparate healthcare cluster maintains a respective schedule that is separate and distinct from other disparate healthcare clusters. For example, healthcare cluster A 214 maintains a schedule that is separate from both healthcare cluster B 216 and healthcare cluster C 218. Moreover, healthcare cluster B 216 maintains a schedule that is separate from healthcare cluster C 218. As a result, a schedule of healthcare cluster A 214 will not include event entries that originate from healthcare clusters B or C. Each of healthcare clusters A, B, and C might represent either a respective healthcare facility; a respective system or organization of healthcare facilities; or a respective department or unit within a healthcare facility.

Disparate healthcare clusters might maintain respective schedules using the same type or brand of scheduling program (i.e., each uses a different copy of the same scheduling software). Alternatively, disparate healthcare clusters might maintain respective schedules using respective scheduling programs (i.e., scheduling software) that are different from one another. In either scenario, the respective scheduling system of a disparate healthcare cluster is separate from scheduling systems of other disparate healthcare clusters. For example, healthcare cluster A 214 includes general scheduling system 215, which is disparate from healthcare scheduling system 217 of healthcare cluster B 216 and from healthcare scheduling system 219 of healthcare cluster C 218. Likewise, healthcare scheduling system 217 is disparate from healthcare scheduling system 219, even though systems 217 and 219 might be using the same type or brand of scheduling software.

Typically, when disparate healthcare clusters maintain separate schedules, it is difficult for a healthcare clinician to receive a consolidated schedule on a client computing device (e.g., mobile computing device or desktop computing device). However, embodiments of the present invention provide a consolidated schedule to client device 220.

In one embodiment, a set of event information describing a healthcare-related event is received at a central repository 222, which receives event information from a plurality of disparate scheduling systems (e.g., 215, 217, and 219). A "central repository" includes a set of networked resources that receives event information and patient medical-record information (e.g., vial statistics) from disparate healthcare clusters and determines how the information should be aggregated and delivered to various client devices. In addition, the central repository receives information from client devices and determines how the information should be delivered to a disparate healthcare cluster.

FIG. 2 depicts that the central repository 222 receives various sets of event information (e.g., 224a, 240a, 228a, and 230a) from disparate healthcare clusters A, B, and C, as well as patient medical-record information 232a from healthcare cluster A. A variety of different rules might be set up within each scheduling system 215, 217, and 219 to control when and how information is sent from a scheduling system to the central repository 222. For example, the set of event information 224a might be automatically sent from scheduling system 215 to the central repository 222 when an event entry is created using a scheduling system 215, such that as depicted in FIG. 2, information 224a is sent independently of other event information (e.g., department schedule) that is also created using scheduling system 215. Alternatively, sets of event information (e.g., 228a and 230a) might be sent together with a schedule 234 of multiple events. For example, a rule might dictate that a schedule is automatically sent from scheduling system 219 to the central repository 222 at set time intervals (e.g., every 12 hours).

FIG. 2 depicts that sets of information 228a and 230a are embedded in a layer of schedule 234. That is, although the depiction of schedule 234 only shows shaded areas 236 and 238, information 228a and 230a is still included within schedule 234 and is sent simultaneously with schedule 234 to the central repository 222. Likewise, schedule 226 might include a set of event information 240a included therewith that describes a shift assignment of Healthcare Clinician "Smith" starting at 10:30 AM. Alternatively, information 228a and 230a might be independently sent, i.e., separate from a department schedule and separate from one another.

Sets 224a, 228a, and 230a each describe an appointment of a patient. For example, set 224a indicates that Dr. Smith is scheduled in Operating Room (OR) ABC on December 31$^{st}$ at 8:00 AM to see a patient named "Miller." Likewise, sets 228a and 230a each depict respective appointments. In contrast, schedule 226 depicts a shift-assignment schedule, which, instead of describing a specific patient appointment, describes a shift assignment of a healthcare clinician (e.g., inpatient rounds from 10:30-13:00). Although schedule 226 only identifies one clinician (Smith), schedule 226 might include assignments for a plurality of healthcare clinicians (e.g., nurses, doctors, etc.). Although sets 224a, 226, 228a, and 230a depict patient appointments and shift assignments, healthcare events might include a variety of other items (e.g., labs, therapy, diagnostic imaging, etc.) that are scheduled using systems 215, 217, or 219.

Each of sets 224a, 228a, 230a, and 240a includes information that describes a particular event. For example, sets 224a, 228a, 230a, and 240a include a date, time, location, and clinician name. A clinician unique identifier (e.g., 225) is usable to determine how event entries should be aggregated, such as after they are received by the central repository 222. Likewise, a patient unique identifier (e.g., 227) might be used to request or aggregate patient records, as will be described in further detail below.

The central repository 222 also receives patient information (e.g., information 232a) from each of the disparate sources. For example, each healthcare cluster might include an electronic-medical-record system 213 that pushes patient information to network 212 and to the central repository 222. Patient information might include a variety of information, such as vital statistics and lab results. Customizable rules might also dictate when patient information is provided to central repository. For example, vital statistics might be provided to network 212 in real time or at set intervals.

As previously described, network 212 facilitates communication between clusters A, B, and C and client 220. For example, network 212 might include a medical information computing system environment 20 that was described with respect to FIG. 1. Network 212 includes the central repository 222, which receives, separates, and aggregates event entries and patient information into appropriate groups. That is, central repository 222 includes a set of computer-executable instructions 223 that, when executed by a computing device, enable the central repository 222 to receive, separate, and aggregate event entries (e.g., 224a) and patient information (e.g., 232a)

FIG. 2 depicts that information 224a, 228a, 230a, 232a and 240a is received by network 212, and in one embodiment, is received by the central repository 222. The central repository 222 determines how sets of information should be aggregated. For example, the central repository might aggregate sets of information based on a healthcare clinician associated therewith or based on a healthcare cluster from which the information was sent.

Table 242 illustrates how information might be organized after being aggregated by central repository. Table 242 includes columns under which certain sets of information are organized. For example, column 244 includes information related to healthcare cluster A 214, column 246 includes information related to Dr. Lee, and column 248 includes information related to Dr. Smith. The information organized under each column represents a version of copy of information sets 224*a*, 228*a*, 230*a*, 232*a* and 240*a*. For example, information 224*b* organized under column 244, and information 224*b'* organized under 248, represent different copies of information set 224*a*. Likewise, information sets 232*b* and 232*b'* represent different copies of information set 232*a*, and information sets 230*b*, 228*b*, and 240*b* represent copies of 230*a*, 228*a*, and 240*a* respectively.

Table 242 also represents an aggregation of information sets received from disparate systems. For example, column 248 includes information sets 224*b'*, 228*b*, 240*b*, and 232*b'*, which have been organized in an aggregation relevant to "Dr. Smith." Information sets 224*b'*, 228*b*, 240*b*, and 232*b* might be filtered and aggregated using various methods, such as by identifying a unique identifier 225 of Dr. Smith that is included with each of the information sets. Although not depicted in FIG. 2, each disparate system might use a different unique identifier to identify a same healthcare clinician. For example, system 215 might identify Dr. Smith using one unique identifier (e.g., "ABC789"), whereas system 219 uses a completely different unique identifier (e.g., "ZZZ321"); however, central repository 222 recognizes that both unique identifiers are associated with Dr. Smith.

Other methods might be utilized to organize and aggregate events. In one embodiment, events are associated with a patient. For example, sets 224*a* and 232*a* include a unique identifier of a patient. Accordingly, events might be aggregated according to a patient, such that a copy (not shown) of 224*a* and 232*a* are stored in a grouping related to "Miller." The aggregated events could then be searched using names and/or unique identifiers of clinicians that have an association with the patient.

In a further embodiment, the central repository 222 packages aggregated event entries to be sent to the client 220. For example, event entries organized under column 248 for Dr. Smith include sets 224*b'*, 228*b*, and 240*b*. As such, event entries 224*b'*, 228*b*, and 240*b* might be transformed into a consolidated schedule 262*a* or otherwise packaged to enable client 220 to present a consolidated view of 224*b*, 228*b*, and 240*b*. The consolidated schedule 262*a* includes information 224*c*, 228*c*, and 240*c*, which represent versions of 224*b'*, 228*b*, and 240*b* (respectively) after being transformed into the consolidated schedule 262*a*. The consolidated schedule 262*a* also includes information 232*c* (i.e., medical information of patient "Miller"), which has been deemed relevant to the event entry identified in information set 224*c* (i.e., appointment of "Miller" with Dr. Smith).

After client 220 has been authenticated to verify that a user (e.g., healthcare clinician) of the client 220 is authorized to view the consolidated schedule 262*a*, a copy of the consolidated schedule 262*b* is provided to the client 220. For example, the consolidated schedule 262*b* might be provided as a web page or using an application (e.g., mobile application) running on the client 220. Alternatively, the consolidated schedule 262*b* might be communicated in a format that allows an application running on client 220 to populate the items into an already existing calendar.

Various rules might be established to dictate when the consolidated schedule 262*b* is provided to client 220. For example, the consolidated schedule 262*b* might be provided upon receiving a request from client 220. That is, client 220 might submit a request when navigating to a secure web page that presents the consolidated webpage. In this respect, network 212 functions as a content provider or content server providing a most up-to-date version of the consolidated schedule 262*b*. Alternatively, the consolidated schedule 262*b* might be provided to (i.e., pushed to) client 220 in real time. That is, the consolidated schedule 262*b* schedule might be provided to client 220 whenever an event entry is created by a healthcare cluster and received by the network 212. In another embodiment, the consolidated schedule 262*b* might be provided at set intervals. For example, the consolidated schedule 262*b* might be provided 12 hours prior to a schedule's start (i.e., the consolidated schedule for Dec. $31^{st}$ might be received at noon on Dec. $30^{th}$).

FIG. 2 illustrates a screenshot 260 that presented on a display of client 220. Screenshot 260 depicts a consolidated schedule 262*c* that includes event entries 224*d*, 228*d*, and 240*d*. Event entries 224*d*, 228*d*, and 240*d* represent sets 224*a-c*, 228*a-c*, and 240*a-c* (respectively) after being received by the central repository 222, aggregated, transformed into a single view, and provided to the client 220. As such, consolidated schedule 262*c* allows a user of client 220 to view in a single calendar event entries that originated from disparate scheduling systems.

Screenshot 260 might have various formats depending on what type of client device is utilized. For example, screenshot 260 might include a mobile version for easier presentation by mobile devices or a classic version for presentation by a desktop device. A presentation of 224*d*, 228*d*, and 240*d* might only include select details, such as the location of the appointment and patient name. Accordingly, selecting each event entry allows a user to drill down into more specific details.

In a further embodiment, event entries 224*d*, 228*d*, and 240*d* are selectable, such as by using a touch screen, mouse, or other input device, thereby allowing a user of client 220 to view details of an event entry or take other actions. For example, when event entry 224*d* is selected, additional details 224*e* included in set 224*a* might be presented. In addition, selecting event 224*d* might trigger a request to the central repository 222 to provide patient information 232*d* (a copy of 232*c*) relevant to event 224*d*. As previously indicated, information 232*d* is deemed relevant to event 224*d* (such as by matching patient id's and clinician id's), such that receiving from client 220 a selection of event entry 224*d* prompts network 212 to provide patient information 232*d*. In this respect, the central repository 222 enables client 220 to view both event entries and patient information from disparate scheduling systems.

In another embodiment, when an event entry 224*d*, 228*d*, or 240*d* is selected, a user of client device 220 can execute other actions relevant to the entry, such as rescheduling an event, entering notes relevant to the event, or creating another event (e.g., order labs or other diagnostics). For example, after selecting event entry 224*d*, a clinician might view patient information 232*d* and determine that the appointment scheduled for 8:00 AM on December $31^{st}$ should be rescheduled or that additional labs should be drawn prior to the appointment. As such, the clinician can use client device 220 to send a request to reschedule or a lab-order request. The request (represented by item 264*a*) is sent by the client device 220 and received by network 212. For example, the request 264*a* might be filtered through the central repository 222. The central repository 222 determines to which healthcare cluster the request should be routed and forwards the request to the appropriate healthcare cluster. For example, request 264*b* is a copy of request 264*a* and is organized under column 244 related to healthcare cluster A 214. As such, the invention allows the clinician to execute actions (e.g., send requests to reschedule or lab-order requests) to a plurality of disparate systems through a consolidated schedule, as opposed to having to visit a respective schedule of each system. Rescheduling an appointment and ordering labs are provided as examples of actions that can be taken by a healthcare clinician; however, in practice these actions include a variety of other actions, such as note entry, medication ordering, etc.

Figure 3:
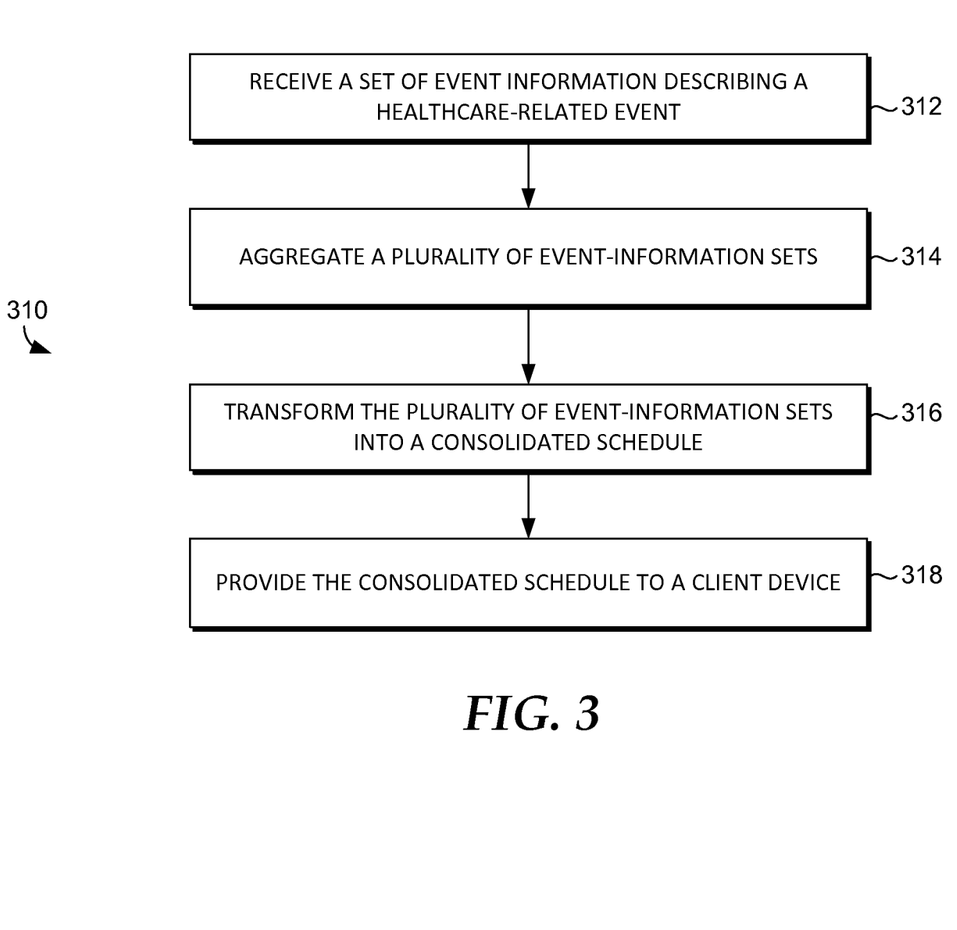
FIGS. 3-5 include flow diagrams, each of which depicts a method in accordance with an embodiment of the present invention.
Figure 4:
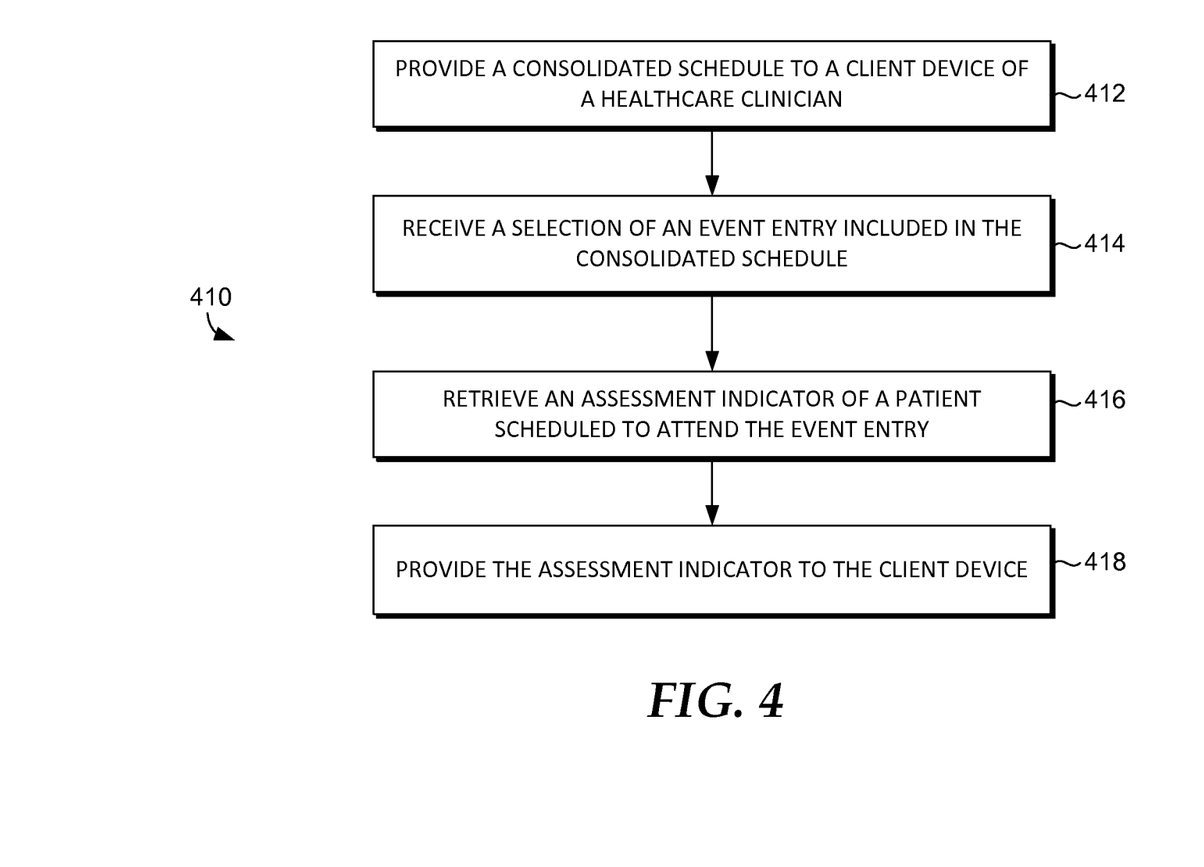
Figure 5:
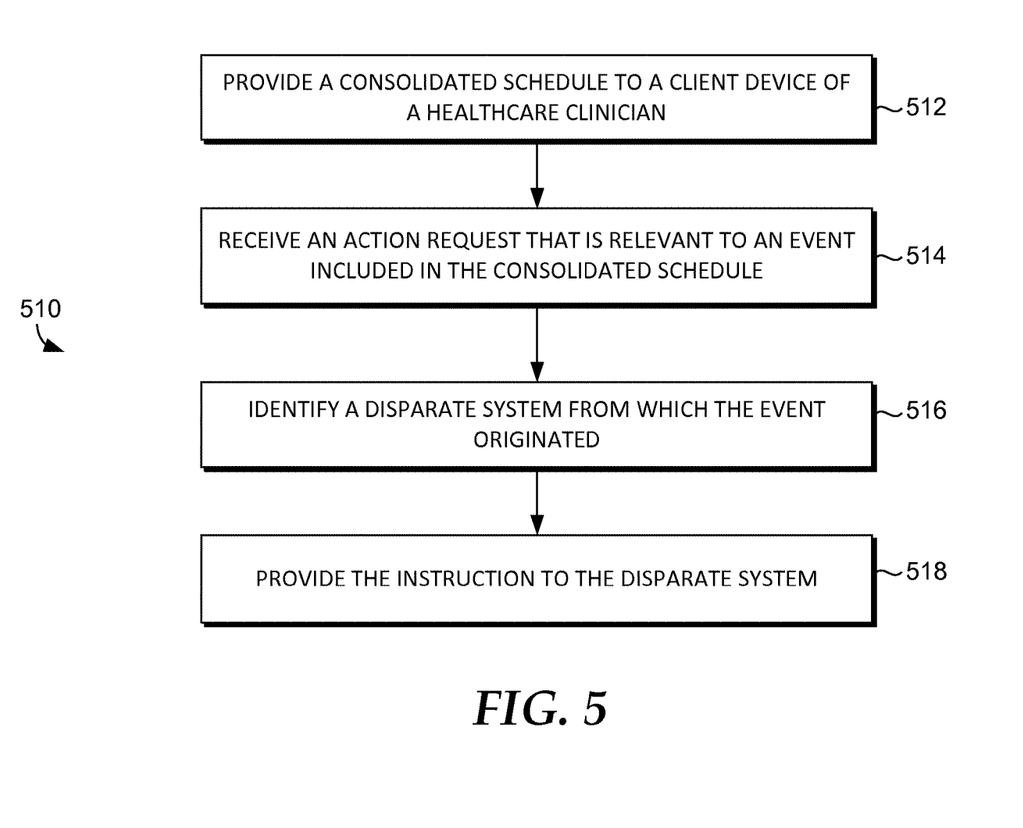

Referring now to FIGS. 3-5, flow diagrams depict various methods that are identified generally by reference numerals 310, 410, and 510. When describing methods 310, 410, and 510, reference might also be made to FIG. 2 for illustrative purposes. Methods 310, 410, and 510 are useful to provide a consolidated schedule having event entries that originate from disparate scheduling systems. For example, network 212 provides consolidated schedule 262b having event entries 224c, 228c, and 240c that originate from disparate scheduling systems associated with healthcare clusters A, B, and C.

Step 312 of method 310 includes receiving, at a central repository, a set of event information describing a healthcare-related event, wherein the central repository receives event information from a plurality of disparate systems. For example, the central repository 222 receives the set 224a that describes an appointment, and the central repository 222 also receives other event information (e.g., 232a, 228a, 230a, and 240a) from disparate systems (e.g., scheduling systems and EMR system) associated with healthcare clusters A, B and C.

Step 314 includes aggregating a plurality of event-information sets, each of which describes a respective medical-related event and each of which is received from a respective system of the plurality of disparate systems. For example, event-information sets 224a, 228a, and 240a are received from respective scheduling systems 214, 216, and 218. The central repository aggregates the information sets by identifying a common identifier (e.g., unique clinician identifier and/or unique patient identifier) and associating the sets with one another. For example, sets 224b', 228b, and 240b are organized together under column 248.

Step 316 includes transforming the plurality of event-information sets into the consolidated schedule, and at step 318, the consolidated schedule is provided to a client device. For example, sets 224b, 228b, and 240b are transformed to consolidated schedule 262a. The consolidated schedule (represented as items 262b) might be provided as a web page to client device 220, the web page presenting screenshot 260.

Referring now to FIG. 4, a flow diagram depicts another method in accordance with an embodiment of the invention that is generally identified by reference numeral 410. Method 410 includes at step 412 providing a consolidated schedule to a client device of a healthcare clinician, wherein the consolidated schedule includes a set of event entries, each of which originated from a respective system of a plurality of disparate systems. For example, as previously described, sets 224b, 228b, and 240b might be populated into a single consolidated schedule 262a. The consolidated schedule (represented as item 264b) might be provided as a web page to client device 220, the web page presenting screenshot 260.

At step 414, method 410 includes receiving from the client device a selection of an event entry from among the set of event entries, wherein the event entry describes a healthcare-related event. For example, a healthcare clinician might select event entry 224d using a touch screen, mouse, or other input device, which in turn causes network 212 to receive from client 220 an indication that event entry 224d was selected. As previously described, event entry 224d describes an appointment of a patient.

Method 410 includes, at step 416, retrieving an assessment indicator that suggests a functioning level of a patient scheduled to attend the healthcare-related event. For example, network 212 might retrieve patient information 232c, which includes a blood-pressure measurement of patient "Miller," which is scheduled to attend the event identified by event entry 224d. As previously described, upon receiving information 232a, the central repository 222 determines relevance to event entry 224a, such as by matching clinician id and/or patient id, thereby allowing retrieval of the patient information 232c when a selection of event entry 224d is received.

At step 418, the assessment indicator is provided to the client device to be presented with event information that described the healthcare-related event. For example, information 232d, which represents a copy of assessment indicator 232a, is provided to client 220 together with event details 224e related to event entry 224d.

Referring now to FIG. 5, a flow diagram depicts another method in accordance with an embodiment of the invention that is generally identified by reference numeral 510. Method 510 includes at step 512 providing a consolidated schedule to a client device, wherein the consolidated schedule includes a set of event entries, each of which originated from a respective system of a plurality of disparate systems. For example, as previously described, sets 224b, 228b, and 240b might be populated into a single consolidated schedule 262a. The consolidated schedule (represented as item 264b) might be provided as a web page to client device 220, the web page presenting screenshot 260.

Step 514 includes receiving from the client device an action request that is relevant to an event identified by an event entry included in the set of event entries. For example, network 212 receives from client device 220 information 264a, which includes a request (e.g., request to reschedule or lab-order request) relevant to an event identified by event entry 224d.

At step 516, central repository identifies a disparate system from among a plurality of disparate systems from which the event entry originated. For example, the central repository 222 might identify a disparate-system unique identifier (not shown) that is included in request 264a and that matches an identifier of healthcare cluster A. As such, a copy 264b of the request organized under column 244 related to healthcare cluster A. At step 516, the instruction to reschedule is communicated to the disparate system. For example, a copy of request 264b might be sent to the generic scheduling system 215 of healthcare cluster A.

Many different arrangements of the various components depicted, as well as components not shown, are possible without departing from the scope of the claims below. Embodiments of our technology have been described with the intent to be illustrative rather than restrictive. Alternative embodiments will become apparent readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. Non-transitory computer-readable media storing computer-executable instructions that, when executed, perform a method of providing a consolidated schedule having event entries that originate from disparate systems, the method comprising:

receiving, at a central repository, a plurality of event-information sets from a plurality of disparate systems, wherein each event-information set received includes (1) a scheduled healthcare-related event for a patient, (2) a time for the scheduled healthcare-related event to occur, and (3) a single clinician identifier for the scheduled healthcare-related event;

using the single clinician identifier as a filter, generating a subset of event-information sets from among the plurality of event-information sets, the subset of event-information sets corresponding to scheduled healthcare-related events for a plurality of patients, each event-information set of the subset including the single clinician identifier;

transforming the subset of event-information sets corresponding to scheduled healthcare-related events for a plurality of patients and including the single clinician identifier into a computing format usable by a calendar application run on a client device to populate an events calendar with the subset of event-information sets, wherein the subset of event-information sets are arranged into a consolidated schedule as transformed, wherein a consolidated view presents a view of, in a single calendar of the calendar application, the scheduled healthcare-related events originating from the plurality of disparate systems;

receiving authentication data that verifies the calendar application run on the client device is authorized to receive the consolidated schedule, wherein the authentication data is associated with a clinician corresponding to the single clinician identifier;

automatically pushing the consolidated schedule to the calendar application run on the client device, the consolidated schedule including the scheduled healthcare-related events of the plurality of patients and times for the scheduled healthcare-related events to occur corresponding to the subset of event-information sets;

when a new scheduled healthcare-related event of an event-information set is received from one or more of the plurality of disparate systems and which includes the single clinician identifier, subsequently transforming the new scheduled healthcare-related event into the computing format that is usable by the client device that runs the calendar application and arranging the new scheduled healthcare-related event into an updated consolidated schedule as transformed; and automatically pushing the updated consolidated schedule to the calendar application run on the client device.

2. The computer-readable media of claim 1, wherein each system of the plurality of disparate systems is controlled by a respective healthcare financial institution.

3. The computer-readable media of claim 1, wherein each system of the plurality of disparate systems is controlled by a respective department within a healthcare facility.

4. The computer-readable media of claim 1 wherein generating a subset of event-information sets from among the plurality of event-information sets further comprises determining that a clinician corresponding to the single clinician identifier is scheduled for the healthcare-related events of the plurality of patients, the healthcare-related events corresponding to the event-information sets of the subset.

5. The computer-readable media of claim 1, wherein the plurality of healthcare-related events includes a surgery schedule of a healthcare facility and wherein generating a subset of event-information sets from among the plurality of event-information sets includes identifying one or more healthcare-related events that are included in the surgery schedule.

6. The computer-readable media of claim 1, wherein the plurality of healthcare-related events includes a shift-assignment schedule of a healthcare-facility department and wherein generating a subset of event-information sets from among the plurality of event-information sets includes identifying one or more healthcare-related events that are included in the shift-assignment schedule.

7. The computer-readable media of claim 1, wherein each system uses a scheduling application having a respective information structure, and wherein each respective information structure is different from other information structures utilized by other systems.

8. A method of automatically updating a calendaring application, the method comprising:

receiving, at a central repository, an event-information set, wherein the event-information set describes (1) a scheduled healthcare-related event for a patient, (2) a time for the scheduled healthcare-related event to occur, (3) a first clinician identifier of a clinician corresponding to the scheduled healthcare-related event for the patient, and (4) a first patient identifier of the patient;

receiving, at the central repository, a second patient identifier of the patient and a diagnosed condition of the patient derived from an electronic-medical-record system that is separate from the calendaring application run on the client device;

matching the first patient identifier derived from the event-information set to the second patient identifier derived from the electronic-medical-record system;

based on matching the first patient identifier to the second patient identifier, combining the event-information set and the diagnosed condition of the patient derived from the electronic-medical-record system;

using the combined event-information set and the diagnosed condition, creating an event entry for the scheduled healthcare-related event for the patient based on the time for the scheduled healthcare-related event to occur and including the diagnosed condition, and further storing the first clinician identifier in association with the event entry;

transforming the event entry into a computing format that is usable by the calendaring application run on the client device to populate the event entry into an events calendar, wherein the events calendar of the calendaring application is a single calendar view of a plurality of entry events originating from a plurality of disparate systems;

receiving authentication data that includes a second clinician identifier and that verifies the client device that runs the calendaring application is authorized to receive the event entry;

based on matching the first clinician identifier to the second clinician identifier of the authentication data, providing the transformed event entry to the calendaring application run on the client device for populating the events calendar, the event entry including:

(1) the scheduled healthcare-related event for the patient based on the time for the scheduled healthcare-related event to occur derived from the calendaring application run on the client device, and (2) the diagnosed condition derived from the electronic-medical-record system, wherein the event entry is selectable in the events calendar to display, via the client device, the diagnosed condition and the scheduled healthcare-related event; and when a new scheduled healthcare-related event of a new event-information set, having the first clinician identifier of the clinician, is received, transforming the new event entry into the computing format that is usable by the calendaring application and automatically pushing the new transformed event entry to the calendaring application run on the client device for populating the events calendar.

9. The method of claim 8, wherein the first patient identifier and the second patient identifier are the same.

10. The method of claim 8, wherein the first clinician identifier and the second clinician identifier are not the same.

11. A method of automatically updating a calendar application, the method comprising:

receiving, at a central repository, a plurality of event-information sets from a plurality of disparate systems, wherein each event-information set in the plurality includes (1) a scheduled healthcare-related event for a patient, (2) a time for the scheduled healthcare-related event to occur, and (3) a single clinician identifier for the scheduled healthcare-related event;

using the single clinician identifier as a filter, generating a subset of event-information sets from among the plurality of event-information sets, the subset of event-information sets corresponding to scheduled healthcare-related events for a plurality of patients, each event-information set of the subset including the single clinician identifier;

transforming the subset of event-information sets corresponding to scheduled healthcare-related events for a plurality of patients and including the single clinician identifier into a computing format that is usable by the calendar application run on a client device to populate the subset of event-information sets into an events calendar, wherein the subset of event-information sets are arranged into a consolidated schedule as transformed, wherein the consolidated schedule is a single calendar view of a plurality of scheduled healthcare-related events originating from the plurality of disparate systems, and wherein the consolidated schedule is specific to a clinician corresponding to the single clinician identifier;

receiving authentication data that is associated with the clinician corresponding to the single clinician identifier and that verifies the calendar application run on the client device is authorized to receive the consolidated schedule;

based on the authentication data received, updating the calendar application run on the client device by automatically pushing the consolidated schedule to the calendar application run on the client device when the consolidated schedule is formatted, the consolidated schedule including the scheduled healthcare-related events for the plurality of patients of the subset including the single clinician identifier;

each time a new scheduled healthcare-related event is received from one or more of the plurality of disparate systems and includes the single clinician identifier, subsequently transforming the new scheduled healthcare-related event into the computing format that is usable by the client device that runs the calendar application and arranging the new scheduled healthcare-related event into an updated consolidated schedule as transformed; and automatically pushing the updated consolidated schedule to the calendar application run on the client device.

12. The method of claim 11, wherein each of the respective healthcare-related events corresponding to the subset of event-information sets is scheduled with the clinician corresponding to the single clinician identifier.

13. The method of claim 11, wherein the plurality of healthcare-related events includes a surgery schedule of a healthcare facility and wherein generating a subset of event-information sets from among the plurality of event-information sets includes identifying one or more healthcare-related events that are included in the surgery schedule.

14. The method of claim 11, wherein the plurality of healthcare-related events includes a shift-assignment schedule of a healthcare-facility department and wherein generating a subset of event-information sets from among the plurality of event-information sets includes identifying one or more healthcare-related events that are included in the shift-assignment schedule.

15. The method of claim 11, wherein each system uses a scheduling application having a respective information structure, and wherein each respective information structure is different from other information structures utilized by other systems.

* * * * *